US008668647B2

(12) United States Patent
Eskandari et al.

(10) Patent No.: US 8,668,647 B2
(45) Date of Patent: Mar. 11, 2014

(54) BANDPASS SAMPLING FOR ELASTOGRAPHY

(75) Inventors: Hani Eskandari, Vancouver (CA); Ali Baghani, Vancouver (CA); Septimiu Edmund Salcudean, Vancouver (CA); Robert N. Rohling, Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 13/213,111

(22) Filed: Aug. 19, 2011

(65) Prior Publication Data

US 2012/0095323 A1 Apr. 19, 2012

Related U.S. Application Data

(60) Provisional application No. 61/393,362, filed on Oct. 15, 2010.

(51) Int. Cl.
*A61B 8/00* (2006.01)
(52) U.S. Cl.
USPC .......................................... 600/437; 382/128

(58) Field of Classification Search
USPC ........................... 600/437–469; 382/128–132
See application file for complete search history.

(56) References Cited

U.S. PATENT DOCUMENTS

| 6,815,179 | B2 * | 11/2004 | Ochi et al. | 435/41 |
| 2008/0033297 | A1 * | 2/2008 | Sliwa | 600/439 |
| 2010/0256530 | A1 * | 10/2010 | Varghese et al. | 600/587 |
| 2012/0123304 | A1 * | 5/2012 | Rybyanets | 601/2 |

* cited by examiner

*Primary Examiner* — Sanjay Cattungal

(57) ABSTRACT

The characterization of tissue viscoelastic properties requires the measurement of tissue displacements over a region of interest at frequencies that exceed significantly the frame rates of conventional medical imaging devices. The present invention involves using bandpass sampling to track high-frequency tissue displacements. With this approach, high frequency signals limited to a frequency bandwidth can be sampled and reconstructed without aliasing at a sampling frequency that is lower than the Nyquist rate. With bandpass sampling, it is feasible to use conventional beam-forming on diagnostic ultrasound machines to perform high frequency dynamic elastography. The method is simple to implement as it does not require beam interleaving, additional hardware or synchronization and can be applied to magnetic resonance elastography.

17 Claims, 10 Drawing Sheets

BANDPASS SAMPLING FOR ELASTOGRAPHY

CROSS REFERENCE TO RELATED APPLICATION

This application claims priority under 35 U.S.C. §119(e) to a U.S. provisional application having Ser. No. 61/393,362, filed Oct. 15, 2010, the entirety of which is herein incorporated by reference.

FIELD OF THE INVENTION

The present invention relates to a method for imaging high-frequency tissue motion using bandpass sampling.

BACKGROUND OF THE INVENTION

Elastography is a technique to measure the mechanical properties of soft tissue in order to detect pathological or anatomical changes. For this purpose, an imaging modality such as ultrasound or magnetic resonance imaging (MRI) is typically used to capture tissue displacements due to an externally applied excitation. The measured displacements are then analyzed to estimate the mechanical properties such as elasticity, viscosity, shear wave speed, Poisson's ratio or non-linear tissue parameters. The quasi-static and low-frequency compression schemes, although proven to be effective in many cases, cannot provide quantitative estimates of the viscoelastic parameters without accurate knowledge of boundary forces. In order to obtain absolute values of the mechanical properties, dynamic or transient elastography solutions have been proposed in prior art. In some of these methods, such as those described in U.S. Pat. No. 7,731,661 to Salcudean et al. and in U.S. patent application Ser. No. 12/240,895 to Salcudean et al. and in U.S. patent application Ser. No. 12/611,736 to Eskandari et al. the entirety of each of which is hereby incorporated by reference, a mechanical exciter induces a dynamic motion field in soft tissue while an ultrasound machine tracks the motion of the tissue due to that exciter. In dynamic elastography, a steady-state excitation is applied to the tissue and the steady-state wave patterns at specific frequencies are observed.

A major limitation of conventional medical imaging devices, such as ultrasound and MRI, is that the image acquisition frame rate is small relative to the excitation frequency that is required for dynamic elastography purposes.

In order to address this limitation in magnetic resonance elastography, the motion sensitive gradient is generally synchronized with the harmonic excitation to sample at equally spaced time intervals. This method is described in U.S. Pat. No. 6,486,669 to Sinkus et al. the entirety of which is hereby incorporated by reference. Therefore, the imaging mechanism is phase locked to the harmonic excitation waveform and can reproduce the actual motion pattern. This method requires accurate synchronization between the imaging device (which is MRI in this case) and the excitation. Another drawback of this technique is that it only allows sampling of the waveform at particular instances within every period.

In ultrasound elastography, one can increase the imaging frame-rate by scanning a small region and repeating the procedure until the entire region of interest is scanned (as used for example in a journal paper by Nightingale, et al. "On the feasibility of remote palpation using acoustic radiation force", in Journal of the Acoustical Society of America, vol. 110, no. 1, pp. 625-634, 2001). Alternatively, to sample high frequency tissue motion using an ultrasound machine, a different scheme for data acquisition, processing or transducer pulse sequencing can be employed. In a paper by Brekke, et al. in 2004 ("Increasing frame rate in ultrasound imaging by temporal morphing using tissue Doppler," in Proceedings of the IEEE Ultrasonics Symposium, pp. 118-121) morphing is used to produce additional frames between successive acquired frames. The velocity data obtained from the ultrasound data is used in the morphing algorithm. Although this method helps the clinicians by increasing the display update rate, it does not overcome the inherent Nyquist limit for measuring high-frequency components of tissue motion. Another approach to high-frame-rate ultrasound imaging is to use non-conventional pulsing techniques. One of these techniques which was entitled Explososcan and discussed in a paper by Shattuck, et al. in 1984 ("Explososcan: A parallel processing technique for high speed ultrasound imaging with linear phased arrays," Journal of Acoustical Society of America, vol. 75, no. 4, pp. 1273-1282) is based on transmitting an unfocused ultrasound pulse such as one with a linear wave front. The pulse illuminates the entire region to be imaged. Parallel receive beam-forming is then performed to reconstruct the radio frequency (RF) data and B-mode images. In another paper by J. Lu in 1997 ("2D and 3D high frame rate imaging with limited diffraction beams", in IEEE Transactions in Ultrasonics, Ferroelectrics & Frequency Control, vol. 44, no. 4, pp. 839-856), the inverse Fourier transform was used to construct an ultrasound image from such transmitted and received plane or linear wave fronts. Fink et al. in 2002 (Ultra high speed imaging of elasticity", in IEEE Ultrasonics Symposium, pp. 1811-1820), proposed the use of ultrafast ultrasound which is a similar technique based on unfocused transmission and parallel receive beam-forming. In a paper by Baghani et al. in 2004 ("A high frame rate ultrasound system for the study of tissue motions", in IEEE Transactions in Ultrasonics, Ferroelectrics & Frequency Control, vol. 57, no. 7, pp. 1535-1547), the entirety of which is hereby incorporated by reference, a high frame-rate ultrasound technique based on beam-interleaving and sectoring of the original field of view is proposed. Additional phase correction was implemented to compensate for the phase difference between adjacent sectors.

The techniques developed in the past few decades are based on complicated hardware and data processing. One of the deficiencies of such methods, implemented for example on ultrasound, is that the resulting ultrasound images are of reduced quality compared to a conventional ultrasound data acquisition scheme with sequential A-line acquisition. However, a conventional ultrasound machine which can acquire sequential A-lines at a lower frame-rate cannot track tissue motion at high frequencies using any of the prior art methods. Prior art methods do not enable capturing of high frequency tissue motion with conventional medical imaging devices which is for example required for measuring the absolute values of the mechanical properties. Measurement of the absolute values of tissue mechanical properties generally requires a vibration frequency of at least 25 Hz and thus a minimum sampling rate of 50 Hz which cannot be achieved on a conventional ultrasound machine unless by lowering the quality of the images. It is beneficial to be able to measure tissue displacements with a conventional imaging device that creates images sequentially without resorting to much reduced sizes of regions of interest. Also, an MRI machine cannot acquire tissue displacements with an arbitrary waveform at any sampling frequency.

Consequently, there exists a need for a method that addresses one or more deficiencies in the prior art. The present invention enables the measurement of high-frequency tissue displacements which is otherwise impossible using a relatively low frame-rate imaging device.

BRIEF SUMMARY OF THE INVENTION

In accordance with the invention, dynamic elastography and imaging high frequency tissue displacements with a low frame-rate medical imaging device, such as an ultrasound or a magnetic resonance imaging machine is possible by using bandpass sampling.

The method according to some embodiments comprises measuring tissue displacements that are generated in response to a vibration signal. Tissue displacements are measured by means of an imaging device that has a sampling frequency lower than two times the maximum frequency component in the tissue displacements. Tissue displacements can be single frequency or multi-frequency. In some embodiments, tissue displacements can have band-limited frequency spectra.

The method according to some embodiments comprises measuring tissue displacements that are generated in response to a vibration signal wherein the vibration signal has at least one sinusoidal waveform in its spectrum. Tissue displacements are measured by means of an imaging device. Further, at least one pair of consecutive measurements of the tissue displacements in at least one location at which the displacements are measured occurs at a time difference larger than one half the smallest period in the vibration signal.

The method according to some other embodiments comprises measuring tissue displacements that are generated in response to a vibration signal wherein the vibration signal comprises at least one sinusoidal waveform with a frequency above 25 Hz. Tissue displacements are measured by means of an imaging device. Further, at least one pair of consecutive measurements of the tissue displacements in at least one location occurs at a time difference larger than one half the smallest period in the vibration signal.

In one embodiment, the displacements within a region of interest are measured before the displacements within that region of interest are measured a second time.

Tissue displacements can be measured by fitting a model comprising at least one sinusoidal waveform. Consequently, a linear system of equation can be solved to measure tissue displacements.

The imaging device can be an ultrasound machine, a magnetic resonance imaging machine, an optical coherence tomography machine or any other machine that enables tracking and measuring tissue displacements. Methods to measure tissue displacement phasors in situations where the sampling frequency of the imaging device is constant or the sampling frequency is time-varying are described in different embodiments. The invention can be used to facilitate elasticity imaging of soft tissue of humans or soft tissue of animals.

The system according to some embodiments employs a method as described in other embodiments of the invention and further comprises a vibration source to generate a vibration signal and an imaging device to measure tissue displacements.

BRIEF DESCRIPTION OF THE DRAWINGS

In the accompanying drawings, which illustrate one or more exemplary embodiments.

DETAILED DESCRIPTION OF THE PREFERRED EMBODIMENTS

Figure 1:
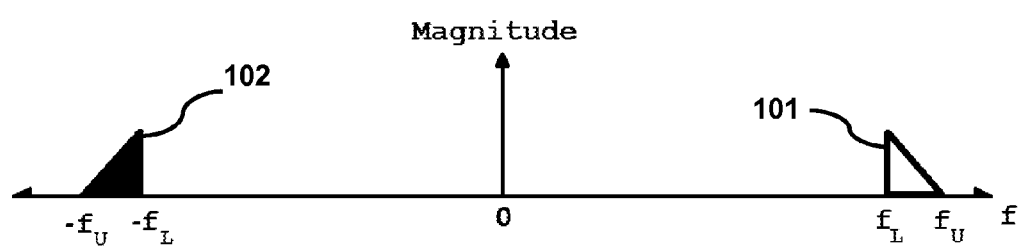
FIG. 1, FIG. 2 and FIG. 3 depict an example of the spectrum of a signal that has been sampled with two bandpass sampling frequencies.

This invention comprises the use of bandpass sampling in dynamic elastography. Through using bandpass sampling, soft tissue can be characterized at frequencies that are even higher than the frame rate of the imaging device which can be an ultrasound or a magnetic resonance imaging machine. In one embodiment, this can be useful when a real-time map of the viscoelastic parameters (including elasticity or viscosity) at a relatively high frequency is desired. Due to the impracticality of demodulating the displacement data in imaging modalities such as ultrasound or magnetic resonance elastography, bandpass sampling can provide a means to image high frequency motion without having to change the conventional imaging settings. One inventive aspect of using bandpass sampling for elastography is that accurate synchronization with the excitation pulse is not required and also a multi-frequency or narrow-band excitation can also be applied. The correct choice of the sampling frequency that can be used with this invention and the preferred methods to interpret the bandpass sampled displacements are disclosed in the following description.

Accurate quantitative measurement of the viscoelastic properties of soft tissue requires dynamic excitation to be applied at frequencies high enough such that the wavelength in the medium would be comparable to the dimensions that have to be resolved within the tissue or specimen. Through bandpass sampling of the displacement waveforms, dynamic elastography will not be substantially limited to the frame rate of the underlying imaging modality. For example, the conventional operation of most of the commercially available ultrasound machines does not allow imaging tissue displacements at frame rates higher than 50 Hz, unless the imaging sector size or the line density of the image are reduced. Based on the conventional theory of sampling, a frame rate of 50 Hz limits the maximum allowable excitation frequency to be the Nyquist rate of 25 Hz. However, bandpass sampling enables one to increase the excitation frequency significantly and to measure tissue displacements which contain frequencies above 25 Hz. As a result, measurement of absolute values of tissue mechanical properties would be feasible.

What is herein meant by tissue is, but not limited to, any soft tissue of a human body or any soft tissue of an animal body, imaged in vivo or in-vitro. As well, tissue can mean any material that can be imaged by a medical imaging device, and that may or may not be designed and manufactured to mimic actual tissue.

In one embodiment of the invention, the tissue is imaged by an ultrasound machine wherein radio frequency data are acquired from a plurality of locations within tissue at a plurality of times. In this embodiment, tissue displacements are measured by tracking the motion in the RF data acquired from one time instance with respect to another RF data from a previous time instance. In one aspect of this embodiment, the displacements are measured between every two RF data acquired consecutively in time from the same location in the tissue. Tissue displacements that are obtained with this method are herein called relative tissue displacements. In another aspect of this embodiment, the displacements are measured with respect to a reference RF data frame which remains unchanged until several tissue displacements are measured. Tissue displacements that are obtained with this method are herein called absolute tissue displacements. What is herein meant by tissue displacements can be, but not limited to, relative tissue displacements or absolute tissue displacements. What is herein meant by one pair of consecutive measurements at one location is the displacement at the specified location which is measured at two consecutive time instances. Also, consecutive measurement hereby means the same as one pair of consecutive measurements. What is herein meant by region of interest is a region within the imaging window in which the tissue displacements are measured. Tissue displacements can be measured for a plurality of locations within the imaging window. This plurality of locations constitutes the region of interest. Furthermore, what is herein meant by one of said plurality of locations is one location in the region of interest at which tissue displacements are measured.

Representing a signal in the frequency domain is achieved through the well-known Fourier transform. In this approach, a continuous-time signal can be expanded as the sum of infinite sinusoids with different frequencies, amplitudes and phases. The Fourier transform of a signal $x_c(t)$ is defined as:

$$X_c(jf) = \int_{-\infty}^{+\infty} x_c(t) e^{-j2\pi ft} dt, \quad (1)$$

where f is the frequency in the continuous domain and j is the imaginary unit. The representation of the complex values of displacements at one frequency using an amplitude and a phase component or a real and an imaginary component is called phasor. Sampling the continuous-time signal at regular intervals (T) is identical to convolving it with a train of Dirac delta functions:

$$x(n) = x_c(nT) = \sum_{n=-\infty}^{+\infty} x_c(t) \delta(nT - t), \quad (2)$$

where $\delta(t)$ is a function that integrates to one and equals to zero everywhere, except at t=0. From (1), the Fourier transform of the discrete-time signal x(n) is:

$$X(f) = \int_{-\infty}^{+\infty} \left[ \sum_{n=-\infty}^{+\infty} x_c(t) \delta(nT - t) \right] e^{-j2\pi ft} dt = \quad (3)$$

$$\sum_{n=-\infty}^{+\infty} \int_{-\infty}^{+\infty} x_c(t) \delta(nT - t) e^{-j2\pi ft} dt$$

$$\Rightarrow X(f) = \sum_{n=-\infty}^{+\infty} x(n) e^{-j2\pi fnT}.$$

Here, X(f) represents the discrete-time Fourier transform of x(n). The sampling frequency can be defined as $f_s=1/T$; hence, $$X(f) = \sum_{n=-\infty}^{+\infty} x(n) e^{-j2\pi fn/f_s}. \quad (4)$$

Note that X(f) is a band-limited and periodic function of frequency, thus $X(f+f_s)=X(f)$. At a given frequency, X(f) is a phasor with amplitude and phase components. According to the conventional sampling theory, in order to be able to perfectly reconstruct a band-limited continuous signal from its discrete-time samples, the minimum required sampling frequency is twice the maximum frequency present in the continuous signal.

Figure 2:
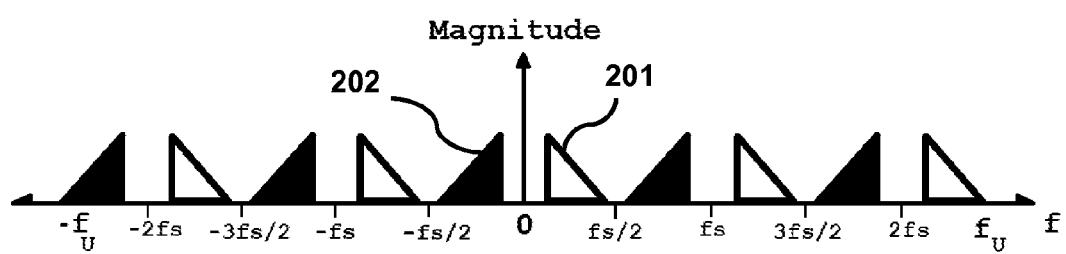
Figure 3:
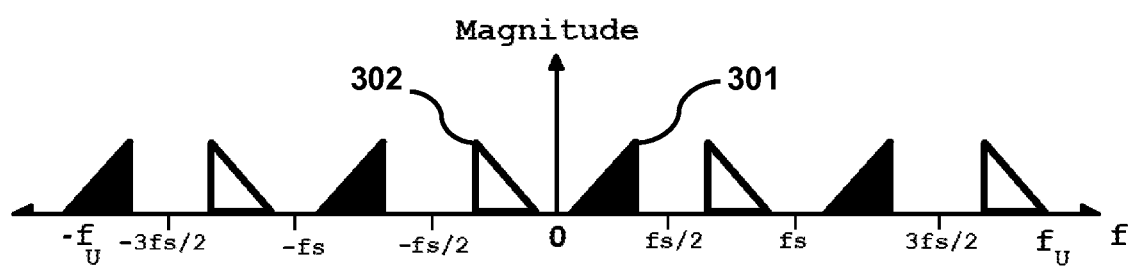

Under certain conditions, a continuous bandpass signal can be sampled at frequencies that are much lower than two times its highest frequency component and the signal still can be reconstructed correctly. A bandpass signal is a signal which has a lowest spectral frequency which is above zero and a highest spectral frequency which is finite. The difference of the highest and the lowest spectral frequencies of a bandpass signal is the bandwidth of that signal. By properly choosing the sampling frequency based on the bandwidth of the bandpass signal and its lowest and highest spectral frequencies, overlapping of the aliased frequency components can be avoided. The theory of bandpass sampling is presented in (Waters and Jarrett, "Bandpass signal sampling and coherent detection," in IEEE Transactions on Aerospace and Electronic Systems, vol. AES-18, no. 6, pp. 731-736, November 1982) the entirety of which is hereby incorporated by reference. As an example, FIG. 1 shows the spectrum of a continuous-time bandpass signal positive spectral lobe 101 and negative spectral lobe 102. This spectrum is then undersampled in order to obtain the repetitive spectral components. One major criterion to consider while performing bandpass sampling is to have $f_s>2B$, where B is the positive bandwidth of the signal ($B=f_u-f_L$). This holds under the assumption that the sampled signal is real and therefore its positive and negative spectral lobes are the mirror conjugates of each other. In FIG. 2, the process of under-sampling resulted in the positive and negative lobes being shifted by multiples of $f_s$. In this case, no overlap has occurred between the spectral components and the low-frequency modulated version of the original signal can be reconstructed by an appropriate lowpass filter to obtain the baseband modulated positive lobe 201 and negative lobe 202. A different choice of $f_s$ for the same spectrum in FIG. 3 results in a misplacement of the positive spectral lobe 302 and negative spectral lobe 301. However, given that aliasing did not occur, the signal can still be reconstructed perfectly from the available baseband information.

Figure 4:
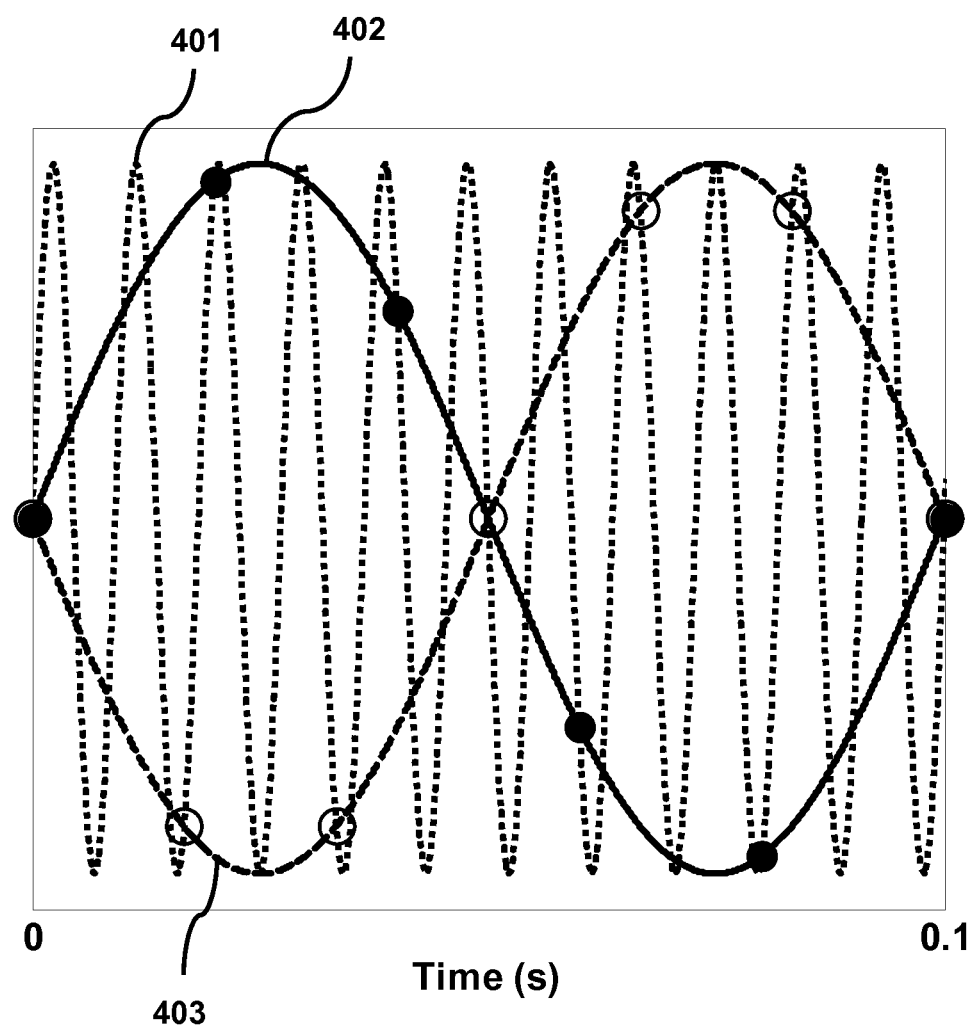
FIG. 4 depicts a 110 Hz signal that has been sampled at 50 Hz and 60 Hz.

FIG. 4 shows a 110 Hz sinusoidal waveform 401 which is sampled at 50 Hz and 60 Hz. With a 50 Hz sampling frequency, the spectrum is shifted to 10 Hz which is shown as a thick solid line 402. The phase and the amplitude of this harmonic waveform are identical to the original high frequency sine wave. With a 60 Hz sampling frequency, the spectral inversion happens and the resulting 10 Hz sinusoid demonstrates a phase shift equal to π 403.

In order to avoid aliasing at the upper and lower bounds of the spectrum, the acceptable range of the sampling frequency is:

$$\frac{2f_c + B}{m+1} \leq f_s \leq \frac{2f_c - B}{m}, \quad (5)$$

where $f_c$ is the center frequency of the spectrum and B is the positive frequency bandwidth. m is a positive integer which indicates the minimum number of spectral half-shifts ($f_s/2$) required to shift the original spectrum to the baseband. Referring to FIG. 1, $2f_c=2f_L+B=2f_u-B$. Equation (5) can be used with the other condition, $f_s>2B$, to determine if a chosen sampling frequency will cause spectral overlap.

Figure 5:
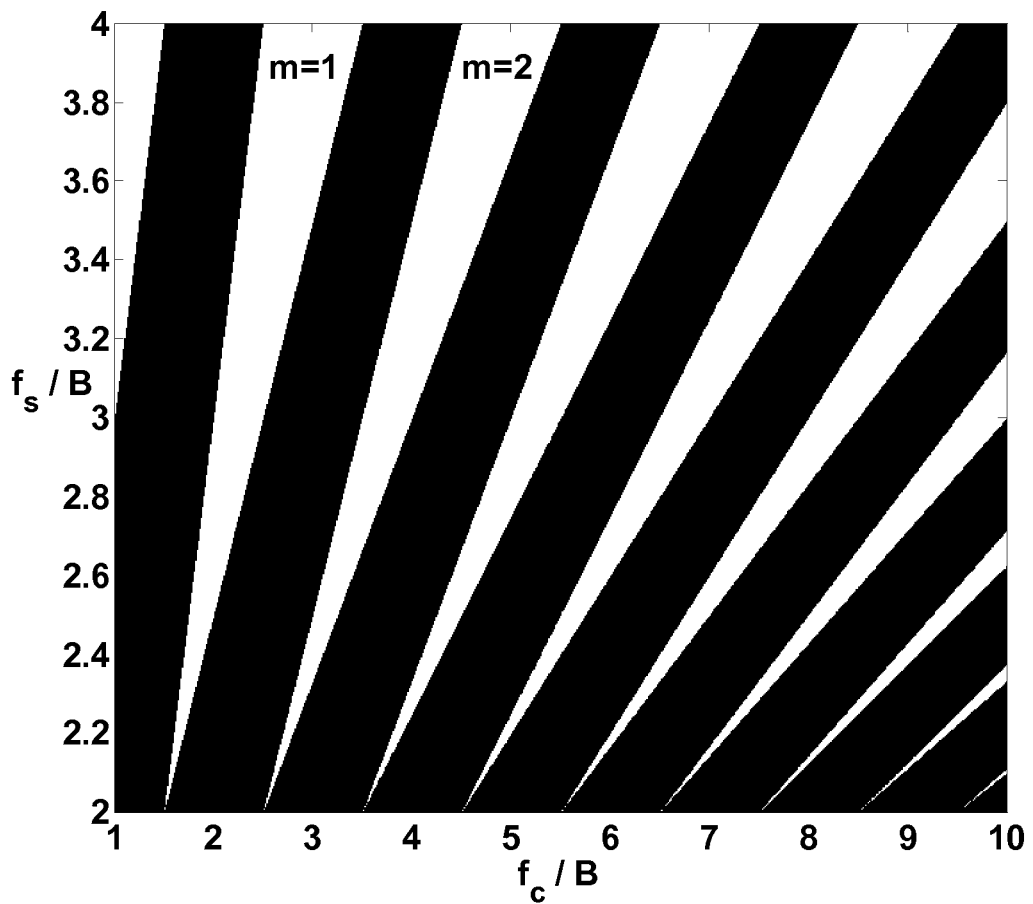
FIG. 5 shows the acceptable range of bandpass sampling frequencies.

The acceptable ranges of $f_s$ constitute a discrete domain. If the center and sampling frequencies are normalized with respect to the bandwidth, the inequality in (5) can be evaluated for different values of m as shown in FIG. 5. The white regions indicate the ranges of acceptable sampling frequency for a given normalized center frequency and the dark areas correspond to the inappropriate frequencies at which aliasing will occur. To avoid spectral overlap, the sampling frequency must be higher than twice the bandwidth.

In order to avoid spectral phase inversion after bandpass sampling, an even number of spectral shifts by $f_s/2$ should take place at positive frequencies due to sampling, thus m should be an even number. Otherwise, the phase of the resulting baseband spectrum should be inverted to obtain the correct continuous signal, and not one that is phase-shifted by $\pi$.

One method to minimize the signal recovery errors due to imperfections in the sampling frequency and bandwidth is to ensure that the original spectrum is shifted to the middle of the baseband frequency range. Therefore based on the lower and upper limits in (5), a reasonable choice for $f_s$ is:

$$f_s = \frac{f_c + B/2}{m+1} + \frac{f_c - B/2}{m}. \tag{6}$$

Figure 6:
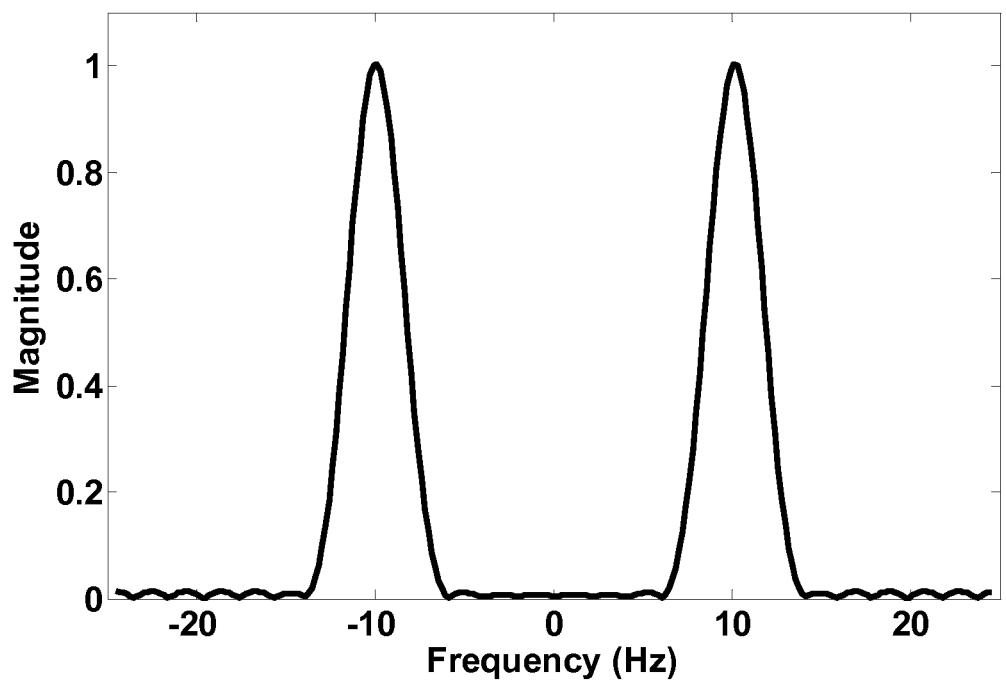
FIG. 6 depicts the windowing effect on the bandwidth of a sinusoidal signal.

Sampling a finite duration signal is identical to multiplying the discrete time-series with a windowing function. Although a rectangular window provides a sharp main-lobe and good resolution at the center frequency, it introduces considerable leakage from the side-lobes. The choice of the windowing function depends on the desired accuracy at the center frequency and the narrowness of the bandwidth. FIG. 6 shows the spectrum of a windowed sinusoid at 10 Hz where a Hamming window was applied. Hamming window and other types of windows are known to experts in the field of signal processing and described in various textbooks on signal processing. Unless the waveform has only one frequency component, the smearing effect of a rectangular window can be significant. In the case of a multi-frequency waveform, the bandwidth of the windowing function determines the maximum detectable resolution.

From FIG. 6, the required guard bands for having no more than 1% interference from the neighboring spectral components can be determined. For this example, for a Hamming window, the bandwidth is 3.8 Hz and the maximum stop-band ripple is 1.4%. If a smaller bandwidth is assumed, more than 1% aliasing may occur due to sampling which will limit the accuracy of the calculations.

The choice of the optimal windowing function depends on the required bandwidth for sampling and the tolerable error for spectral measurements. Due to the windowing effect, a sinusoid will also exhibit a certain bandwidth in the post-sampled spectrum which should be considered when determining the range of valid sampling frequencies.

In elastography, tissue motion is measured as a function of time at a plurality of locations within tissue with a fixed or a varying sampling frequency. By using the method described in the present invention, high frequency tissue motion can be measured by a low frame-rate imaging device such as ultrasound or MRI. If the excitation is band-limited, the sampling frequency of the imaging device has to satisfy the inequality in (5). In one embodiment of this invention, if it is desired to measure the displacement phasors at a certain bandpass frequency, the baseband frequency that corresponds to said bandpass frequency is calculated by subtracting the sampling frequency (which is hereby known as $f_s$) from said bandpass frequency recursively until the resulting baseband frequency is between $-f_s/2$ and $f_s/2$. In this embodiment, after said baseband frequency is calculated, the amplitude of the phasor at said baseband frequency at every location is used as a measure of the amplitude of the displacement phasor at said bandpass frequency. Furthermore, after the baseband frequency is calculated, if the basedband frequency is positive, the phase of the phasor at said baseband frequency at every location is used as a measure of the phase of the displacement phasor at said bandpass frequency. In this embodiment, if the basedband frequency is negative, the inverse of the phase of the phasor at said baseband frequency at every location is used as a measure of the phase of the displacement phasor at said bandpass frequency. Hereby, inverse of the phase means multiplying the phase by negative one.

In one embodiment of this invention, the Fourier transform can be used to calculate the displacement phasors at the excitation frequencies. This way, the bandpass frequencies that correspond to the excitation frequencies are calculated and the phasors at those bandpass frequencies are obtained.

In another embodiment of the invention, where the excitation contains one or more frequencies, the amplitudes and phases for each of the phasors at different frequencies can be found. The displacement $u(x,t)$ at location x and at time t can be written as:

$$u(x, t) = c + \sum_{i=1}^{N} [\alpha_i \sin(2\pi f_i t) + \beta_i \cos(2\pi f_i t)], \tag{11}$$

where N is the number of the sinusoidal waveforms within the vibration signal, each of which is represented by the term within the square brackets in equation (11) and has a frequency equal to $f_i$. $\alpha_i$ and $\beta_i$ are functions of x and depend on the amplitude and phase of the vibration at location x. The reciprocal of $f_i$ is the period ($\tau_i$) of the respective frequency component, meaning that the period of the sinusoidal waveform with frequency $f_i$ is equal to $1/f_i$. The smallest value of all $\tau_i$ for the sinusoidal waveforms which constitute the vibration signal or which constitute $u(x,t)$ in (11) is herein called the smallest period. Also, the smallest frequency value among all $f_i$ is herein called the smallest frequency component and the largest frequency value among all $f_i$ is herein called the largest frequency component. Writing equation (11) for different times:

$$\begin{bmatrix} 1 & \sin(2\pi f_1 t_1) & \cos(2\pi f_1 t_1) & \ldots & \sin(2\pi f_2 t_1) & \cos(2\pi f_N t_1) \\ 1 & \sin(2\pi f_1 t_2) & \cos(2\pi f_1 t_2) & \ldots & \sin(2\pi f_2 t_2) & \cos(2\pi f_N t_2) \\ \vdots & \vdots & \vdots & \ddots & \vdots & \vdots \\ 1 & \sin(2\pi f_1 t_K) & \cos(2\pi f_1 t_K) & \ldots & \sin(2\pi f_2 t_K) & \cos(2\pi f_N t_K) \end{bmatrix} \tag{12}$$

$$\begin{bmatrix} c \\ \alpha_1 \\ \beta_1 \\ \vdots \\ \alpha_N \\ \beta\_N \end{bmatrix} = \begin{bmatrix} u(x, t_1) \\ u(x, t_2) \\ \vdots \\ u(x, t_K) \end{bmatrix}$$

where $t_i$ are the time stamps or time instances of the available displacement time-series. At frequency $f_i$, the amplitude of the vibration is $\sqrt{\alpha_i^2 + \beta_i^2}$ and the phase is $\tan^{-1}(\beta_i/\alpha_i)$. The phase is calculated relative to the phase at $t_1$. The time difference between the second measurement and the first measurement is $t_2-t_1$. The time difference between the $k^{th}$ measurement and the $(k-1)^{th}$ measurement is $t_k-t_{k-1}$.

In a preferred embodiment of the invention, the time points, $t_1, t_2, \ldots, t_K$, at which location x is scanned, are equally spaced in time; thus, $t_2-t_1=t_3-t_2=\ldots=t_K-t_{K-1}$.

If the waveform is sinusoidal with only one frequency component, the bandwidth would be zero and theoretically bandpass sampling can be performed at any frequency. However, since only a finite duration of the sampled waveform can be analyzed, the actual bandwidth will be increased to the spectral bandwidth of the temporal window. Thus, aliasing may still happen if the projected baseband frequency is close to zero or close to half the sampling frequency. Also, in case of limited precision in adjusting the center frequency of the applied excitation or the sampling frequency, additional guard-bands should be included for bandwidth considerations.

A range of the sampling frequency is permissible for bandpass sampling of a waveform with a given center frequency and bandwidth. However, the presence of undesired frequency components is often inevitable, mostly due to the mechanical resonance of the vibration source or tissue, ambient vibrations or low frequency artifacts. Therefore, the bandpass sampling frequency should be chosen such that the desired portion of the spectrum is not aliased with the undesired components as a result of under-sampling.

The motion of the tissue happens in response to a vibration signal. In one embodiment, the vibration signal is generated by means of a vibration source. Such vibration source can be, for example, a motor or an electromagnetic voice coil that are commercially available or built in-house, and their uses are described in numerous publications and in the referenced literature and patents.

In one embodiment of this invention, an imaging device captures images of tissue. Further, a processor associated with the imaging device computes tissue displacements from the imaging data. In one embodiment the processor is part of the imaging device. In another embodiment of the invention, a processor which is separate from the imaging device computes tissue displacements. Thus, by imaging device, we mean a device capable of acquiring tissue images in any number of ways and associated processor that can access the imaging data to compute displacements.

In one embodiment of the invention, a system which a vibration source applies a vibration signal to tissue to generate tissue displacements. Tissue displacements are then measured by means of an imaging device with a sampling rate lower than the maximum frequency component in the vibration signal. In this embodiment, displacements are measured by using bandpass sampling as described herein.

In one embodiment, the imaging device enables measuring of tissue mechanical properties such as elasticity, viscosity or shear wave speed. A system that images tissue mechanical properties is fully described in U.S. Pat. No. 7,731,661 to Salcudean et al. and in U.S. patent application Ser. No. 12/240,895 to Salcudean et al. and in U.S. patent application Ser. No. 12/611,736 to Eskandari et al. the entirety of each of which is hereby incorporated by reference. In one aspect of this embodiment, such a system comprises a vibration source that applies vibration to tissue. Consequently, tissue displacements are measured by means of an imaging device and tissue mechanical properties are calculated within a region of interest. Further, such mechanical properties may be displayed on a display or may be stored, communicated or used in future computations.

Exemplary embodiment: A PVC phantom with a circular inclusion being approximately 3 times stiffer than the background has been used to test the invention. The dimensions of the phantom were 6.0×5.0×3.5 cm in the axial, lateral and elevational directions, respectively, where axial is along the ultrasound beam, lateral is perpendicular to axial, but within the imaging plane, and elevational is perpendicular to both axial and lateral directions. The region of interest was 4.0 cm axially and 2.2 cm laterally. A single frequency excitation at 120 Hz was applied by a motor to the phantom from the bottom. An L14-5/38 ultrasound linear array transducer was transmitting and receiving 5 MHz RF data from the top. RF data were collected for 250 msec in each case. The lateral resolution of imaging was 40 lines per image. Axial displacements in the region of interest (ROI) have been measured by matching the peaks in the compressed and uncompressed RF signals. The axial displacements were interpolated at one hundred evenly-spaced blocks within each line.

Figure 7:
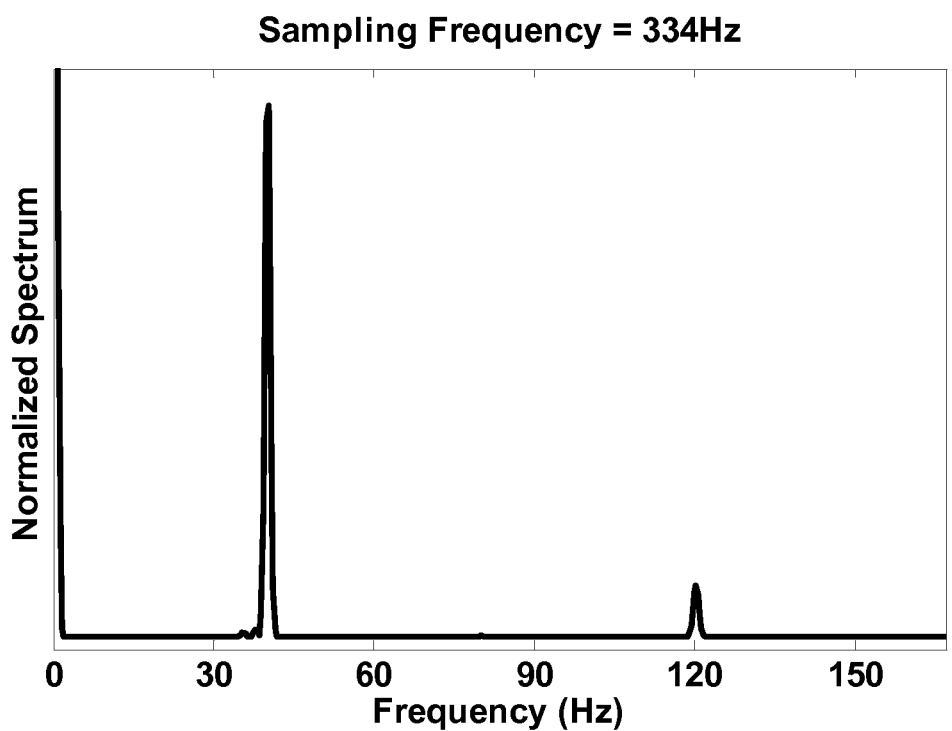
FIG. 7 and FIG. 8 are the spectra of the motion with two different sampling frequencies.
Figure 8:
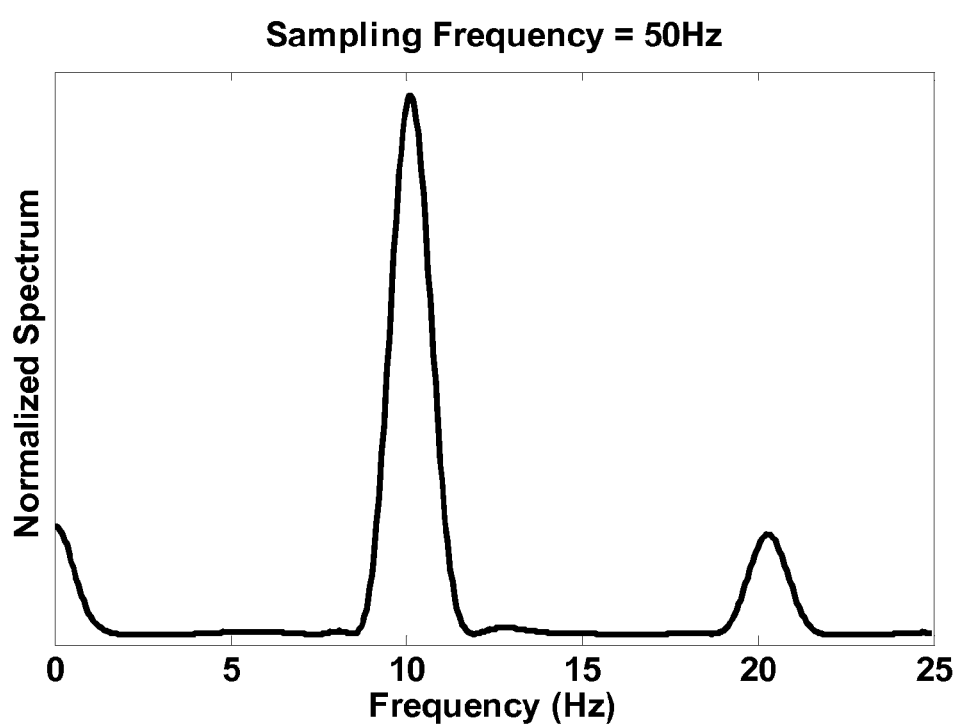

Two tests were performed with different sampling frequencies of the ultrasound machine. In the first test, the sampling frequency was 334 Hz to meet the conventional sampling criterion and be able to capture the full dynamic range of the displacement waveforms at 120 Hz. For the frequency analysis, a Hamming window has been multiplied by the displacements. The Fourier transform of the displacement at a point in the middle of the phantom is shown in FIG. 7. While the 120 Hz component of the excitation is visible in the spectrum, the resonance of the phantom causes an undesired spectral component around 40 Hz with approximately 10 Hz bandwidth. With $f_c=120$ Hz, B=3.8 Hz for a Hamming window, the bandpass sampling frequency can be in the range of 48.8-59.0 Hz for m=1. In another test, the frame rate was set at $f_s=49.86$ Hz. The spectrum of the displacement at a point in the middle of the phantom is shown in FIG. 8. It can be seen that the 120 Hz component is shifted by 2f and appears at 20.3 Hz while the resonance around 40 Hz is translated to around 10 Hz.

Figure 9:
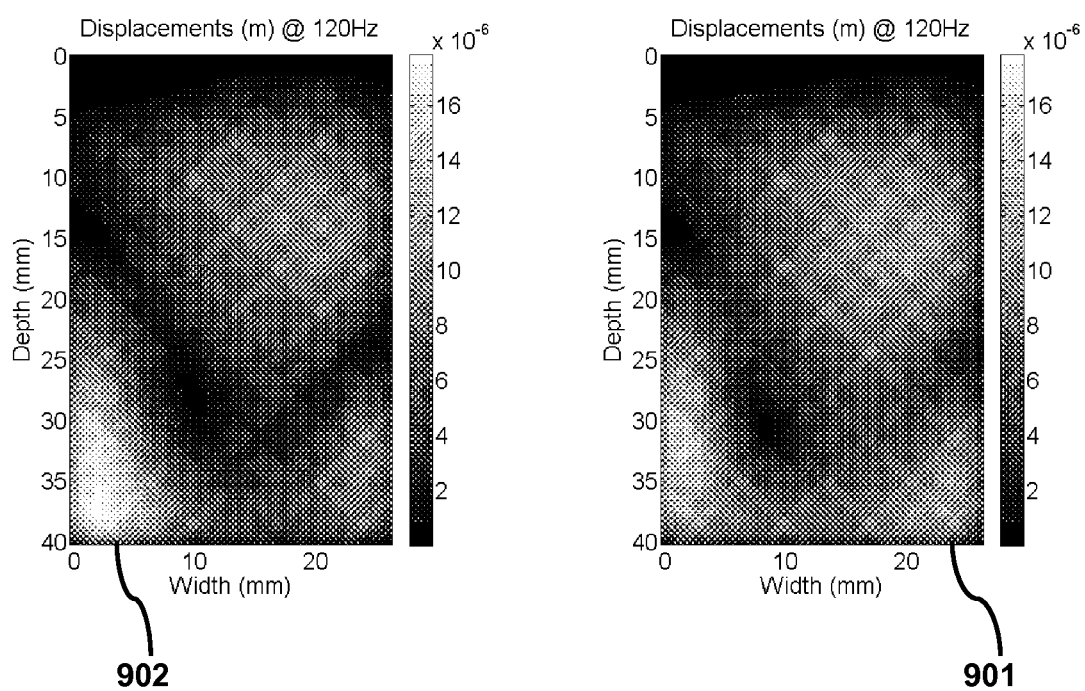
FIG. 9 depicts the displacement amplitude with two different sampling frequencies.

Given that the vibration signal was at 120 Hz and 20.3 Hz respectively in the non-aliased and bandpass cases, the displacement phasors have been calculated at those frequencies for the two tests. The amplitude of the displacement profile is shown in FIG. 9. The steady-state wave pattern in the finite medium produces various peaks and nodes which depend on the material properties, frequency and boundary conditions. It can be seen that the displacement pattern observed by under-sampling at 49.86 Hz 901 is similar to that measured at a sampling frequency of 334 Hz 902.

Figure 10:
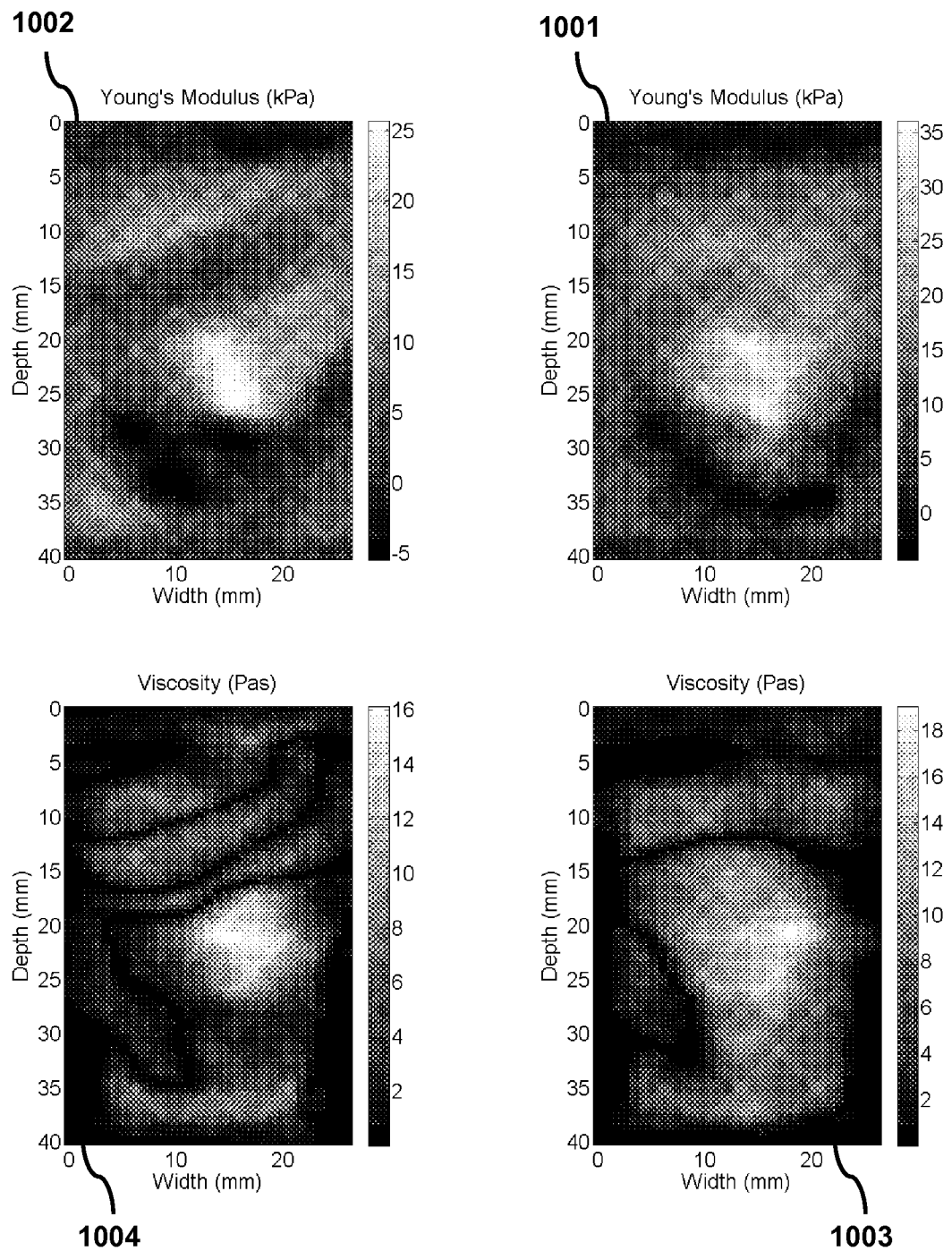
FIG. 10 depicts images of viscosity and elasticity obtained with bandpass sampling and without bandpass sampling.

Using the real and imaginary components of the measured displacements, the inverse problem of elasticity and viscosity was solved using a dynamic finite element method described in the reference patents. The images as shown in FIG. 10 are obtained using the embodiment of the system as described in this invention and in a paper by Eskandari et al. in 2011 ("Bandpass sampling of high-frequency tissue motion", in IEEE Transactions on Ultrasonics, Ferroelectrics & Frequency Control, vol. 58, no. 7) the entirety of which is hereby incorporated by reference. At a sampling frequency of 49.86 Hz, the reconstructed image of elasticity 1001 and viscosity 1003 are shown in FIG. 10. Also, FIG. 10 shows the reconstructed images of the elasticity 1002 and viscosity 1004 at a sampling frequency of 334 Hz.

What is claimed is:
1. A method for measuring phasors of tissue displacements at a plurality of locations, the method comprising:
applying a vibration signal to generate tissue displacements;
measuring tissue displacements by means of an imaging device wherein at least one pair of consecutive measurements of said tissue displacements in at least one loca- tion occurs at a time difference larger than one half the smallest period in said vibration signal; and computing said phasors of tissue displacements using a method selected from the group consisting of (a) computing the Fourier transform of said measurements of tissue displacements, and (b) fitting a model comprising at least one sinusoidal waveform to said measurements of tissue displacements.

2. A method as claimed in claim 1 wherein the imaging device is an ultrasound machine.

3. A method as claimed in claim 1 wherein the imaging device is a magnetic resonance imaging machine.

4. A method as claimed in claim 1 wherein the imaging device is an optical coherence tomography machine.

5. A method as claimed in claim 1 wherein said vibration signal has a band-limited spectrum.

6. A method as claimed in claim 1 wherein the tissue displacements at all locations of said plurality of locations are measured before said displacements at said plurality of locations are measured a second time.

7. A method for measuring phasors of tissue displacements at a plurality of locations, the method comprising:

applying a vibration signal to generate tissue displacements;

measuring said tissue displacements by means of an imaging device at a sampling frequency less than two times the maximum frequency component in the frequency spectrum of said vibration signal; and computing said phasors of tissue displacements using a method selected from the group consisting of (a) computing the Fourier transform of said measurements of tissue displacements, and (b) fitting a model comprising at least one sinusoidal waveform to said measurements of tissue displacements.

8. A method as claimed in claim 7 wherein the sampling frequency of said imaging device is constant.

9. A method as claimed in claim 7 wherein the sampling frequency of said imaging device changes as a function of time.

10. A method as claimed in claim 7 wherein the smallest period in said vibration signal is less than 40 milliseconds.

11. A method as claimed in claim 7 wherein said vibration signal comprises at least one sinusoidal waveform.

12. A method for measuring phasors of tissue displacements at a plurality of locations in response to a vibration signal, said vibration signal comprising at least one sinusoidal waveform with a frequency higher than 25 Hz, the method comprising:

measuring tissue displacements by means of an imaging device wherein at least one pair of consecutive measurements of said tissue displacements in at least one of the plurality of locations occurs at a time difference greater than one half the smallest period in said vibration signal; and computing said phasors of tissue displacements using a method selected from the group consisting of (a) computing the Fourier transform of said measurements of tissue displacements, and (b) fitting a model comprising at least one sinusoidal waveform to said measurements of tissue displacements.

13. A system for measuring tissue displacements employing one of the methods as claimed in claims 1 to 12, the system comprising:

a vibration source for applying vibration to tissue; and an imaging device.

14. A system as claimed in claim 13 wherein the imaging device is an ultrasound machine.

15. A system as claimed in claim 13 wherein the imaging device is a magnetic resonance imaging machine.

16. A system as claimed in claim 13 wherein the imaging device is an optical coherence tomography machine.

17. A method as claimed in claim 12 wherein the tissue displacements at all locations of said plurality of locations are measured before said displacements at said plurality of locations are measured a second time.

* * * * *